(12) United States Patent
Angel et al.

(10) Patent No.: US 7,465,440 B2
(45) Date of Patent: Dec. 16, 2008

(54) PROCESS FOR PREPARING WATER-SOLUBLE OR WATER-DISPERSIBLE POLYETHER-CONTAINING POLYMERS AND THE USE THEREOF AS COATING AGENTS, BINDERS AND/OR FILM-FORMING EXCIPIENTS IN PHARMACEUTICAL DOSAGE FORMS OR PACKAGING MATERIALS OR AS ADDITIVES IN COSMETIC, DERMATOLOGICAL OR HYGIENIC PREPARATIONS

(75) Inventors: Maximilian Angel, Schifferstadt (DE);
Michael Gotsche, Mannheim (DE);
Karl Kolter, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 319 days.

(21) Appl. No.: 09/767,821

(22) Filed: Jan. 24, 2001

(65) Prior Publication Data
US 2001/0018489 A1    Aug. 30, 2001

(51) Int. Cl.
*A61K 31/74* (2006.01)
*A61K 47/00* (2006.01)
(52) U.S. Cl. .............. 424/78.18; 514/772.2; 514/772.4
(58) Field of Classification Search ................ 424/401, 424/78.18; 514/772.2, 772.6
See application file for complete search history.

(56) References Cited

U.S. PATENT DOCUMENTS

| | | | | |
|---|---|---|---|---|
| 2,602,079 A | | 7/1952 | De Groote | 260/89 |
| 3,928,255 A | * | 12/1975 | Milkovich et al. | 260/2.5 |
| 4,085,168 A | * | 4/1978 | Milkovich et al. | 260/886 |
| 4,369,281 A | * | 1/1983 | Zimmermann et al. | 24/379 |
| 5,034,475 A | * | 7/1991 | Kroggel et al. | 525/455 |
| 5,053,455 A | * | 10/1991 | Kroggel et al. | 525/58 |
| 5,134,053 A | * | 7/1992 | Mueller-Hess et al. | 430/176 |
| 5,338,814 A | * | 8/1994 | Wu et al. | 526/210 |
| 5,777,046 A | * | 7/1998 | Boeckh et al. | 525/444 |
| 6,126,970 A | * | 10/2000 | van't Klooster | 424/482 |
| 6,194,125 B1 | * | 2/2001 | Goffing et al. | 430/306 |

FOREIGN PATENT DOCUMENTS

| GB | 922457 | 4/1963 |
|---|---|---|
| GB | 922458 | 4/1963 |
| WO | WO 00/18375 | 4/2000 |

* cited by examiner

*Primary Examiner*—Sreeni Padmanabhan
*Assistant Examiner*—Kantamneni Shobha
(74) *Attorney, Agent, or Firm*—Novak Druce + Quigg LLP

(57) ABSTRACT

A process for preparing graft copolymers of polyvinyl esters by polymerization of
a) at least one vinyl ester of aliphatic $C_1$-$C_{24}$-carboxylic acids in the presence of
b) polyethers which are solid at room temperature and have the general formula I,
c) and, where appropriate, at least one other monomer
using a free-radical organic initiator system, wherein liquid polyalkylene glycol is used as solvent for the free-radical initiator system (feed).

8 Claims, No Drawings

PROCESS FOR PREPARING WATER-SOLUBLE OR WATER-DISPERSIBLE POLYETHER-CONTAINING POLYMERS AND THE USE THEREOF AS COATING AGENTS, BINDERS AND/OR FILM-FORMING EXCIPIENTS IN PHARMACEUTICAL DOSAGE FORMS OR PACKAGING MATERIALS OR AS ADDITIVES IN COSMETIC, DERMATOLOGICAL OR HYGIENIC PREPARATIONS

The invention relates to a process for preparing water-soluble or water-dispersible polyether-containing polymers and to the use thereof as coating agents, binders and/or film-forming excipients in pharmaceutical dosage forms or as additives in cosmetic, dermatological and/or hygienic preparations, and to cosmetic, dermatological, hygienic and/or pharmaceutical compositions comprising the novel polymers.

It is known to prepare graft copolymers by the action of ethylene oxide on polymers with active hydrogen, such as, for example, cellulose, polyamides etc.

U.S. Pat. No. 2,602,079 discloses a process for preparing alkoxylated polymers of vinyl esters. The two-stage process described therein is, however, inconvenient and hazardous and, moreover, uneconomic because of the use of solvents.

DE 1 077 430, DE 1 094 457 and DE 1 081 229 describe processes for preparing graft copolymers of polyvinyl esters and the use thereof as water-soluble packaging films and as auxiliaries in cosmetics.

The cited documents describe the preparation of graft copolymers from polyethylene glycols and vinyl esters (and other comonomers) in . . . general. The corresponding solid polyethylene glycols are in these cases dissolved in the monomeric vinyl esters (where appropriate with the assistance of solvents), and polymerized with the addition of free-radical initiators. Part of the mixture is partially polymerized and then the remainder of the mixture is fed in.

There are considerable safety objections to processes carried out in this way, for example due to the mixing of grafting base, monomer and initiator before the polymerization or in the feed.

It is an object of the present invention to develop a safe process which can also be employed for industrial applications, in which meterability of the free-radical initiator is good, even for small amounts, and which does not have the disadvantages mentioned.

We have found that this object is achieved by a process for preparing graft copolymers of polyvinyl esters by polymerization of a) at least one vinyl ester of aliphatic $C_1$-$C_{24}$-carboxylic acids in the presence of b) polyethers which are solid at room temperature and have the general formula I c) and, where appropriate, at least one other monomer using a free-radical initiator system, wherein a liquid polyalkylene glycol is used as solvent for the free-radical initiator system.

The polymerization can be carried out by conventional polymerization processes. The polymerization can be carried out either in the batch or, preferably as a feed process.

The procedure for polymerization in the batch process can be such that the polyether-containing compound b) is dissolved in at least one monomer of group a) and possibly other comonomers of group c) and, after addition of a polymerization initiator, the mixture is polymerized to completion. In the feed process, the polymerization is carried out semicontinuously by initially mixing a portion, for example 10%, of the mixture for polymerization composed of the polyether-containing compound b), at least one monomer of group a), possibly other comonomers of group c) and initiator, heating the mixture to the polymerization temperature and, after the initiation of the polymerization, adding the remainder of the mixture for polymerization in accordance with the progress of the polymerization. The polymers can also be obtained by introducing the polyether-containing compounds of group b) to a reactor and heating to the polymerization temperature, and adding at least one monomer of group a), preferably other comonomers of group c) and polymerization initiator either all at once, batchwise or, preferably, continuously in parallel with the initiator, and polymerizing.

In contrast with prior art processes, the dissolving of the initiator in liquid polyalkylene glycol ensures safe management of the reaction. The novel process has the further advantage that the introduction of further grafting base leads to improved product properties, no other, i.e. chemically different, solvent is required.

The graft copolymers prepared according to the invention are used as coating agents and binders and/or film-forming excipients in pharmaceutical dosage forms, and in cosmetics.

The solvents employed for the free-radical initiator are polyalkylene glycols which are liquid at room temperature. Their molecular weight is between 88 and 1000, preferably 100 and 600. Polyethylene glycols are particularly preferably employed.

Polyethers which are solid at room temperature mean polyethers of the general formula I

in which the variables have the following meaning, independently of one another:

$R^1$ hydrogen, $C_1$-$C_{24}$-alkyl, $R^9$—C(=O)—, $R^9$—NH—C(=O)—, polyalcohol residue;

$R^8$ hydrogen, $C_1$-$C_{24}$-alkyl, $R^9$—C(=O)—, $R^9$—NH—C(=O)—;

$R^2$ to $R^7$
—(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—, —CH$_2$—CHOR$^{10}$—CH$_2$—;

$R^9$ $C_1$-$C_{24}$-alkyl;

$R^{10}$ hydrogen, $C_1$-$C_{24}$-alkyl, $R^9$—C(=O)—;

A —C(=O)—O—, —C(=O)—B—C(=O)—O—, —C(=O)—NH—B—NH—C(=O)—O—;

B —(CH$_2$)$_r$—, arylene, optionally substituted;

n 1 to 8;

s 0 to 500;

t 1 to 12;

u 1 to 5000;

v 0 to 5000;

w 0 to 5000;

x 1 to 5000;
y 0 to 5000;
z 0 to 5000.

Generally used as grafting base b) for the graft copolymers prepared according to the invention are polyethers of the general formula I selected from the group consisting of polyalkylene oxides based on ethylene oxide, propylene oxide and butylene oxide, and polyglycerol. Depending on the nature of the monomer units, polymers with the following structural units result.

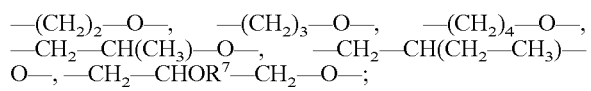

These may be both homopolymers and copolymers, and the copolymers may have a random distribution or be in the form of so-called block copolymers.

Depending on the degree of grafting, the polymers used according to the invention comprise both pure graft copolymers and mixtures of the abovementioned graft copolymers with ungrafted polyethers of the formula I and homo- or copolymers of monomers a) and, where appropriate, other monomers c).

The terminal primary hydroxyl groups of the polyethers prepared on the basis of alkylene oxides or glycerol, and additionally the secondary OH groups of polyglycerol, may be present both in unprotected free form and etherified with alcohols with a $C_1$-$C_{24}$ chain length or esterified with carboxylic acids with a $C_1$-$C_{24}$ chain length, or be reacted with isocyanates to give urethanes.

Alkyl radicals which may be mentioned for $R^1$ and $R^8$ to $R^{10}$ are branched or unbranched $C_1$-$C_{24}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Preferred representatives of the abovementioned alkyl radicals which may be mentioned are branched or unbranched $C_1$-$C_{12}$-, particularly preferably $C_1$-$C_6$-alkyl chains.

The molecular weight of the polyether used as grafting base is in the range from 1000 to 500,000, preferably in the range from 1000 to 100,000, particularly preferably in the range from 1000 to 20,000, very particularly preferably in the range from 1000 to 15,000.

It is advantageous to use homopolymers of ethylene oxide or copolymers with an ethylene oxide content of from 40 to 99% by weight. Thus, the content of ethylene oxide units in the ethylene oxide polymers which are preferably to be employed is from 40 to 100 mol %. Suitable as comonomer for these copolymers are propylene oxide, butylene oxide and/or isobutylene oxide. Suitable examples are copolymers of ethylene oxide and propylene oxide, copolymers of ethylene oxide and butylene oxide, and copolymers of ethylene oxide, propylene oxide and at least one butylene oxide. The ethylene oxide content in the copolymers is preferably from 40 to 99 mol %, the propylene oxide content is from 1 to 60 mol %, and the butylene oxide content in the copolymers is from 1 to 30 mol %. Besides straight-chain it is also possible to use branched homo- or copolymers as grafting base.

It is moreover possible to form polymers in which at least one, preferably one to eight, particularly preferably one to five, of the hydroxyl groups present in the polyalcohols can be linked in the form of an ether linkage to the following polyether residue P as shown in formula I

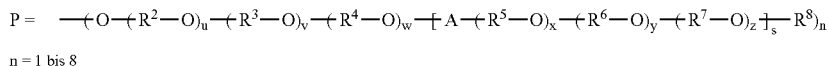

n = 1 bis 8

The alkylene oxide units in the polymer may be randomly distributed or present in the form of blocks.

However, it is also possible to use polyesters of polyalkylene oxides and aliphatic $C_1$-$C_{12}$-, preferably $C_1$-$C_6$-dicarboxylic acids or aromatic dicarboxylic acids, for example oxalic acid, succinic acid, adipic acid or terephthalic acid, with molecular weights of from 1500 to 25,000, described in EP-A-0 743 962, as grafting base.

It is furthermore possible to use polycarbonates of polyalkylene oxides prepared by phosgenation, or else polyurethanes of polyalkylene oxides and aliphatic $C_1$-$C_{12}$-, preferably $C_1$-$C_6$-diisocyanates or aromatic diisocyanates, for example hexamethylene diisocyanate or phenylene diisocyanate, as grafting base.

The abovementioned polyesters, polycarbonates or polyurethanes may comprise up to 500, preferably up to 100, polyalkylene oxide units, it being possible for the polyalkylene oxide units to consist both of homopolymers and of copolymers of various alkylene oxides.

The polymers preferably prepared are those obtainable by polymerization of a) at least one vinyl ester of aliphatic $C_1$-$C_{24}$-carboxylic acids in the presence of b) polyethers which are solid at room temperature and have the general formula I,
   in which the variables have, independently of one another, the following meaning:
   $R^1$ hydrogen, $C_1$-$C_{24}$-alkyl, $R^9$—C(=O)—, polyalcohol residue;
   $R^8$ hydrogen, $C_1$-$C_{24}$-alkyl, $R^9$—C(=O)—;
   $R^2$ to $R^7$
   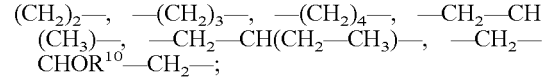
   $R^9$ $C_1$-$C_{24}$-alkyl;
   $R^{10}$ hydrogen, $C_1$-$C_{24}$-alkyl, $R^9$—C(=O)—;
   n 1 to 8;
   s 0;
   u 1 to 5000;
   v 0 to 5000;
   w 0 to 5000 c) and, where appropriate, another monomer,
   using a free-radical initiator system, wherein a liquid polyalkylene glycol is used as solvent for the free-radical initiator system.

The polymers particularly preferably prepared are those obtainable by polymerization of
a) at least one vinyl ester of aliphatic $C_1$-$C_{12}$-carboxylic acids in the presence of
b) polyethers which are solid at room temperature and have the general formula I and an average molecular weight of more than 1000, in which the variables, independently of one another, have the following meaning:
   $R^1$ hydrogen, $C_1$-$C_{12}$-alkyl, polyalcohol residue;
   $R^8$ hydrogen, $C_1$-$C_{12}$-alkyl;
   $R^2$ to $R^7$
      —$(CH_2)_2$—, —$(CH_2)_3$—, —$(CH_2)_4$—, —$CH_2$—CH($CH_3$)—, —$CH_2$—CH($CH_2$—$CH_3$)—, —$CH_2$—$CHOR^{10}$—$CH_2$—;
   $R^{10}$ hydrogen, $C_1$-$C_{12}$-alkyl;
   n 1 to 5;
   s 0;
   u 2 to 2000;
   v 0 to 2000;
   w 0 to 2000
c) and, where appropriate, another monomer,
   using a free-radical initiator system, wherein a liquid polyalkylene glycol is used as solvent for the free-radical initiator system.

The polymers very particularly preferably prepared are those where at least one vinyl ester of aliphatic $C_1$-$C_6$-carboxylic acids, in particular vinyl acetate, is reacted in the presence of polyethers which are solid at room temperature and have the general formula I and an average molecular weight of greater than 1000, preferably from 1000 to 15,000, in which the variables have the following meaning, independently of one another:
   $R^1$, $R^8$
      hydrogen, $C_1$-$C_6$-alkyl, in particular hydrogen;
   $R^2$ to $R^7$
      —$(CH_2)_2$—, —$(CH_2)_3$—, —$CH_2$—CH($CH_3$)—, —$CH_2$—$CHOR^{10}$—$CH_2$—, in particular —$(CH_2)_2$—;
   $R^{10}$ hydrogen, $C_1$-$C_6$-alkyl;
   n 1;
   s 0;
   u 5 to 500;
   v 0 to 500, in particular 0;
   w 0 to 500, in particular 0
c) and, where appropriate, another monomer, using a free-radical initiator system, wherein a liquid polyalkylene glycol is used as solvent for the free-radical initiator system.

However, it is also possible to employ as polyethers silicone derivatives which are solid at room temperature.

Preferred representatives of such polyether-containing silicone derivatives are those comprising the following structural elements:

II $$R^{10}\!-\!Si(R^8)_2\!-\!O\!-\![Si(R^8)_2\!-\!O]_a\!-\![Si(R^8)_2\!-\!O]_b\!-\!Si(R^8)_2\!-\!R^9$$

-continued
where:

$R^9 = CH_3$ or $$\diagdown\!O\!-\![CH_2CH_2O]_c\!-\![CH_2CH(CH_3)O]_d\!-\!R^{11}$$

$R^{10} = CH_3$ or $R^9$ $R^{11} = H, CH_3,$ $$-\!\![Si(R^8)_2\!-\!O]_a\!-\!Si(R^8)_2\!-\!CH_3$$

$$-\!\!(C(=\!O))_e\!-\!R^{13}$$

$R^{13}$ is an organic radical which comprises 1 to 40 carbon atoms and which may comprise amino, carboxyl or sulfonate groups or, in the case where e=0, is also the anion of an inorganic acid, and where the $R^8$ radicals may be identical or different, and either derive from the group of aliphatic hydrocarbons with 1 to 20 carbon atoms, cyclic aliphatic hydrocarbons with 3 to 20 C atoms, are aromatic in nature or are equal to $R^{12}$, where:

$$R^{12} = -(CH_2)_f\!-\!O\!-\![CH_2CH_2O]_c\!-\![CH_2CH(CH_3)O]_d\!-\!R^{11}$$

with the proviso that at least one of the radicals $R^8$, $R^9$ or $R^{10}$ is a polyalkylene oxide-containing radical complying with the above definition, and f is an integer from 1 to 6, a and b are integers such that the molecular weight of the polysiloxane block is between 300 and 30,000, c and d may be integers between 0 and 50 with the proviso that the total of c and d is greater than 0, and e is 0 or 1.

Preferred radicals $R^9$ and $R^{12}$ are those for which the total of c+d is between 5 and 30.

The $R^8$ groups are preferably selected from the following group: methyl, ethyl, propyl, butyl, isobutyl, pentyl, isopentyl, hexyl, octyl, decyl, dodecyl and octadecyl, cycloaliphatic radicals, specifically cyclohexyl, aromatic groups, specifically phenyl or naphthyl, mixed aromatic-aliphatic radicals such as benzyl or phenylethyl, and tolyl and xylyl and $R^{12}$.

Particularly suitable $R^{11}$ radicals are those in which, in the case of $R^{11}$=—$(CO)_e$—$R^{13}$, $R^{13}$ is any alkyl, cycloalkyl or aryl radical which has between 1 and 40 C atoms and may have further ionizable groups such as $NH_2$, COOH, $SO_3H$.

Preferred inorganic $R^{13}$ radicals are in the case where e=0, phosphate and sulfate.

Particularly preferred polyether-containing silicone derivatives are those of the general structure:

$$CH_3\!-\!Si(R^8)_2\!-\!O\!-\![Si(R^8)_2\!-\!O]_a\!-\![Si(R^{12})\!-\!O]_b\!-\!Si(CH_3)_2\!-\!CH_3$$

It is further possible to use as polyethers (b) also homo- and copolymers of polyalkylene oxide-containing ethylenically unsaturated monomers, such as, for example, polyalkylene oxide (meth)acrylates, polyalkylene oxide vinyl ethers, polyalkylene oxide (meth)acrylamides, polyalkylene oxide allylamides or polyalkylene oxide vinylamides. It is, of course, also possible to employ copolymers of such monomers with other ethylenically unsaturated monomers.

However, products of the reaction of polyethyleneimines with alkylene oxides can also be employed as polyether-containing compounds b). The alkylene oxides used in this case are preferably ethylene oxide, propylene oxide, butylene oxide and mixtures of these, particularly preferably ethylene oxide. The polyethyleneimines which can be employed are polymers with number average molecular weights of from 300 to 20,000, preferably 500 to 10,000, very particularly preferably 500 to 5000. The ratio by weight between alkylene oxide and polyethyleneimine employed is in the range from 100:1 to 0.1:1, preferably in the range from 50:1 to 0.5:1, very particularly preferably in the range from 20:1 to 0.5:1.

The following copolymerizable monomers may be mentioned as component a) for the polymerization in the presence of the polyethers of the formula I:

Vinyl esters of aliphatic, saturated or unsaturated $C_1$-$C_{24}$-carboxylic acids such as, for example, formic acid, acetic acid, propionic acid, butyric acid, valeric acid, isovaleric acid, caproic acid, caprylic acid, capric acid, undecylenic acid, lauric acid, myristic acid, palmitic acid, palmitoleic acid, stearic acid, oleic acid, arachic acid, behenic acid, lignoceric acid, cerotic acid and melissic acid.

Vinyl esters of the abovementioned $C_1$-$C_{12}$-carboxylic acids are preferably used, in particular of the $C_1$-$C_6$-carboxylic acids, very particularly preferably vinyl acetate.

It is, of course, also possible to graft copolymerize mixtures of the respective monomers from group a).

The vinyl esters (a) may also be employed in a mixture with one or more ethylenically unsaturated copolymerizable comonomers (c), in which case the content of these additional monomers should be restricted to a maximum of 50% by weight. Contents of from 0 to 20% by weight are preferred. The term ethylenically unsaturated means that the monomers have at least one carbon-carbon double bond which is capable of free-radical polymerization and may be mono-, di-, tri- or tetrasubstituted.

The preferred ethylenically unsaturated comonomers (c) which are additionally employed may be described by the following general formula:

X—C(O)CR$^{15}$=CHR$^{14}$ where

X is selected from the group of radicals —OH, —OM, —OR$^{16}$, NH$_2$, —NHR$^{16}$, N(R$^{16}$)$_2$;

M is a cation selected from the group consisting of: Na$^+$, K$^+$, Mg$^{++}$, Ca$^{++}$, Zn$^{++}$, NH$_4^+$, alkylammonium, dialkylammonium, trialkylammonium and tetraalkylammonium;

the R$^{16}$ radicals may be identical or different and selected from the group consisting of —H, linear or branched-chain $C_1$-$C_{40}$-alkyl radicals, N,N-dimethylaminoethyl, 2-hydroxyethyl, 2-methoxyethyl, 2-ethoxyethyl, hydroxypropyl, methoxypropyl or ethoxypropyl.

R$^{15}$ and R$^{14}$ are selected, independently of one another from the group consisting of: —H, linear or branched-chain $C_1$-$C_8$-alkyl chains, methoxy, ethoxy, 2-hydroxyethoxy, 2-methoxyethoxy and 2-ethoxyethyl.

Representative, but non-limiting, examples of suitable monomers (c) are, for example, acrylic acid or methacrylic acid and their salts, esters and amides. The salts may be derived from any nontoxic metal, ammonium or substituted ammonium counterions.

The esters may be derived from linear $C_1$-$C_{40}$, branched-chain $C_3$-$C_{40}$ or carbocyclic $C_3$-$C_{40}$ alcohols, from multifunctional alcohols having 2 to about 8 hydroxyl groups such as ethylene glycol, hexylene glycol, glycerol and 1,2,6-hexanetriol, from aminoalcohols or from alcohol ethers such as methoxyethanol and ethoxyethanol, (alkyl)polyethylene glycols, (alkyl)polypropylene glycols or ethoxylated fatty alcohols, for example $C_{12}$-$C_{24}$-fatty alcohols reacted with from 1 to 200 ethylene oxide units.

Also suitable are N,N-dialkylaminoalkyl acrylates and methacrylates and N,N-dialkylaminoalkylacrylamides and -methacrylamides of the general formula (III)

$$\begin{array}{c} R^{17} \\ | \\ =\!\!\!\!\underset{\underset{O}{\|}}{C}\!\!-\!\!Z\!-\!R^{19}\!-\!NR^{20}\!-\!R^{21} \\ (R^{18})_g \end{array} \qquad (III)$$

with

R$^{17}$=H, alkyl with 1 to 8 C atoms,

R$^{18}$=H, methyl,

R$^{19}$=alkylene with 1 to 24 C atoms, optionally substituted by alkyl,

R$^{20}$, R$^{21}$=$C_1$-$C_{40}$-alkyl radical,

Z=nitrogen for g=1 or oxygen for g=0.

The amides may be unsubstituted, N-alkyl or N-alkylamino monosubstituted or N,N-dialkylsubstituted or N,N-dialkylaminodisubstituted, in which the alkyl or alkylamino groups are derived from linear $C_1$-$C_{40}$, branched-chain $C_3$-$C_{40}$ or carbocyclic $C_3$-$C_{40}$ units. The alkylamino groups may additionally be quaternized.

Preferred comonomers of the formula III are N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N-[3-(dimethylamino)propyl]methacrylamide and N-[3-(dimethylamino)propyl]acrylamide.

Comonomers (c) which can likewise be used are substituted acrylic acids and salts, esters and amides thereof, with the substituents on the carbon atom being in the two or three position of the acrylic acid, and are selected independently of one another from the group consisting of $C_1$-$C_4$-alkyl, —CN, COOH, particularly preferably methacrylic acid, ethacrylic acid and 3-cyanoacrylic acid. These salts, esters and amides of these substituted acrylic acids can be selected as described above for the salts, esters and amides of acrylic acid.

Other suitable comonomers (c) are allyl esters of linear $C_1$-$C_{40}$, branched-chain $C_3$-$C_{40}$ or carbocyclic $C_3$-$C_{40}$ carboxylic acids, vinyl or allyl halides, preferably vinyl chloride and allyl chloride, vinyl ethers, preferably methyl, ethyl, butyl or dodecyl vinyl ether, vinylformamide, vinylmethylacetamide, vinylamine; vinyllactams, preferably vinylpyrrolidone and vinylcaprolactam, vinyl- or allyl-substituted heterocyclic compounds, preferably vinylpyridine, vinyloxazoline and allylpyridine.

Also suitable are N-vinylimidazoles of the general formula IV, in which $R^{22}$ to $R^{24}$ are, independently of one another, hydrogen, $C_1$-$C_4$-alkyl or phenyl:

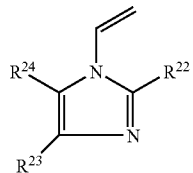

(IV)

Further suitable comonomers (c) are diallylamines of the general formula (V)

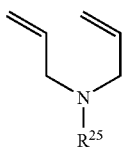

(V)

with $R^{25}$=$C_1$-$C_{24}$-alkyl.

Further suitable comonomers (c) are vinylidene chloride; and hydrocarbons with at least one carbon-carbon double bond, preferably styrene, alpha-methylstyrene, tert-butylstyrene, butadiene, isoprene, cyclohexadiene, ethylene, propylene, 1-butene, 2-butene, isobutylene, vinyltoluene, and mixtures of these monomers.

Particularly suitable comonomers (c) are acrylic acid, methacrylic acid, ethylacrylic acid, methyl acrylate, ethyl acrylate, propyl acrylate, n-butyl acrylate, isobutyl acrylate, t-butyl acrylate, 2-ethylhexyl acrylate, decyl acrylate, methyl methacrylate, ethyl methacrylate, propyl methacrylate, n-butyl methacrylate, isobutyl methacrylate, t-butyl methacrylate, 2-ethylhexyl methacrylate, decyl methacrylate, methyl ethacrylate, ethyl ethacrylate, n-butyl ethacrylate, isobutyl ethacrylate, t-butyl ethacrylate, 2-ethylhexyl ethacrylate, decyl ethacrylate, stearyl (meth)acrylate, 2,3-dihydroxypropyl acrylate, 2,3-dihydroxypropyl methacrylate, 2-hydroxyethyl acrylate, hydroxypropyl acrylates, 2-hydroxyethyl methacrylate, 2-hydroxyethyl ethacrylate, 2-methoxyethyl acrylate, 2-methoxyethyl methacrylate, 2-methoxyethyl ethacrylate, 2-ethoxyethyl methacrylate, 2-ethoxyethyl ethacrylate, hydroxypropyl methacrylates, glyceryl monoacrylate, glyceryl monomethacrylate, polyalkylene glycol (meth)acrylates, unsaturated sulfonic acids such as, for example, acrylamidopropanesulfonic acid;

acrylamide, methacrylamide, ethacrylamide, N-methylacrylamide, N,N-dimethylacrylamide, N-ethylacrylamide, N-isopropylacrylamide, N-butylacrylamide, N-t-butylacrylamide, N-octylacrylamide, N-t-octylacrylamide, N-octadecylacrylamide, N-phenylacrylamide, N-methylmethacrylamide, N-ethylmethacrylamide, N-dodecylmethacrylamide, 1-vinylimidazole, 1-vinyl-2-methylvinylimidazole, N,N-dimethylaminomethyl (meth)acrylate, N,N-diethylaminomethyl (meth)acrylate, N,N-dimethylaminoethyl (meth)acrylate, N,N-diethylaminoethyl (meth)acrylate, N,N-dimethylaminobutyl (meth)acrylate, N,N-diethylaminobutyl (meth)acrylate, N,N-dimethylaminohexyl (meth)acrylate, N,N-dimethylaminooctyl (meth)acrylate, N,N-dimethylaminododecyl (meth)acrylate, N-[3-(dimethylamino)propyl]methacrylamide, N-[3-(dimethylamino)propyl]acrylamide, N-[3-(dimethylamino)butyl]methacrylamide, N-[8-(dimethylamino)octyl]methacrylamide, N-[12-(dimethylamino)dodecyl]methacrylamide, N-[3-(diethylamino)-propyl]methacrylamide, N-[3-(diethylamino)propyl]acrylamide;

maleic acid, fumaric acid, maleic anhydride and its monoesters, crotonic acid, itaconic acid, diallyldimethylammonium chloride, vinyl ethers (for example: methyl, ethyl, butyl or dodecyl vinyl ether), vinylformamide, vinylmethylacetamide, vinylamine; methyl vinyl ketone, maleimide, vinylpyridine, vinylimidazole, vinylfuran, styrene, styrenesulfonate, allyl alcohol, and mixtures thereof.

Of these, particular preference is given to acrylic acid, methacrylic acid, maleic acid, fumaric acid, crotonic acid, maleic anhydride and its monoesters, methyl acrylate, methyl methacrylate, ethyl acrylate, ethyl methacrylate, n-butyl acrylate, n-butyl methacrylate, t-butyl acrylate, t-butyl methacrylate, isobutyl acrylate, isobutyl methacrylate, 2-ethylhexyl acrylate, stearyl acrylate, stearyl methacrylate, N-t-butylacrylamide, N-octylacrylamide, 2-hydroxyethyl acrylate, hydroxypropyl acrylates, 2-hydroxyethyl methacrylate, hydroxypropyl methacrylates, alkylene glycol (meth)acrylates, styrene, unsaturated sulfonic acids such as, for example, acrylamidopropanesulfonic acid, vinylpyrrolidone, vinylcaprolactam, vinyl ethers (for example: methyl, ethyl, butyl or dodecyl vinyl ether), vinylformamide, vinylmethylacetamide, vinylamine, 1-vinylimidazole, 1-vinyl-2-methylimidazole, N,N-dimethylaminomethyl methacrylate and N-[3-(dimethylamino)-propyl]methacrylamide; 3-methyl-1-vinylimidazolium chloride, 3-methyl-1-vinylimidazolium methyl sulfate, N,N-dimethylaminoethyl methacrylate, N-[3-(dimethylamino)propyl]methacrylamide quaternized with methyl chloride, methyl sulfate or diethyl sulfate.

Monomers with a basic nitrogen atom may moreover be quaternized in the following way:

Suitable for quaternizing the amines are, for example, alkyl halides with 1 to 24 C atoms in the alkyl group, for example methyl chloride, methyl bromide, methyl iodide, ethyl chloride, ethyl bromide, propyl chloride, hexyl chloride, dodecyl chloride, lauryl chloride and benzyl halides, in particular benzyl chloride and benzyl bromide. Further suitable quaternizing agents are dialkyl sulfates, in particular dimethyl sulfate or diethyl sulfate. Quaternization of the basic amines can also be carried out with alkylene oxides such as ethylene oxide or propylene oxide in the presence of acids. Preferred quaternizing agents are: methyl chloride, dimethyl sulfate or diethyl sulfate.

The quaternization can be carried out before the polymerization or after the polymerization.

In addition, the products of the reaction of unsaturated acids such as, for example, acrylic acid or methacrylic acid with a quaternized epichlorohydrin of the general formula (VI) can be employed ($R^{26}$=$C_1$-$C_{40}$-alkyl).

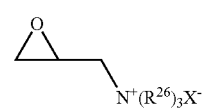

(VI)

Examples thereof are, for example: (meth)acryloyloxyhydroxypropyltrimethylammonium chloride and (meth)acryloyloxyhydroxypropyltriethylammonium chloride.

The basic monomers may also be cationized by neutralizing them with mineral acids such as, for example, sulfuric acid, hydrochloric acid, hydrobromic acid, hydriodic acid, phosphoric acid or nitric acid, or with organic acids such as, for example, formic acid, acetic acid, lactic acid or citric acid.

In addition to the abovementioned comonomers, it is possible to employ as comonomers (c) so-called macromonomers such as, for example, silicon-containing macromonomers with one or more groups capable of free-radical polymerization, or alkyloxazoline macromonomers as described, for example, in EP 408 311.

It is further possible to employ fluorine-containing monomers, as described, for example, in EP 558423, in compounds with a crosslinking action or a regulating effect on molecular weight, in combination or alone.

Regulators which can be used are the conventional compounds known to the skilled worker, such as, for example, sulfur compounds (for example: mercaptoethanol, 2-ethylhexyl thioglycolate, thioglycolic acid or dodecyl mercaptan), and tribromochloromethane or other compounds which have a regulating effect on the molecular weight of the resulting polymers.

It is also possible where appropriate to employ thiol-containing silicone compounds.

Silicone-free regulators are preferably employed.

Crosslinking monomers which can be employed are compounds with at least two ethylenic double bonds, such as, for example, esters of ethylenically unsaturated carboxylic acids such as acrylic acid or methacrylic acid and polyhydric alcohols, ethers of at least dihydric alcohols, such as, for example, vinyl ethers or allyl ethers. Also suitable are straight-chain or branched, linear or cyclic aliphatic or aromatic hydrocarbons which have at least two double bonds which, in the case of aliphatic hydrocarbons, must not be conjugated. Also suitable are amides of acrylic and methacrylic acid and N-allylamines of at least difunctional amines, such as, for example, 1,2-diaminoethane, 1,3-diaminopropane. Also suitable are triallylamine or corresponding ammonium salts, N-vinyl compounds of urea derivatives, at least difunctional amides, cyanurates or urethanes. Further suitable crosslinkers are divinyldioxane, tetraallylsilane or tetravinylsilane.

Examples of particularly preferred crosslinkers are methylenebisacrylamide, triallylamine and triallylammonium salts, divinylimidazole, N,N'-divinylethyleneurea, products of the reaction of polyhydric alcohols with acrylic acid or methacrylic acid, methacrylic esters and acrylic esters of polyalkylene oxides or polyhydric alcohols which have been reacted with ethylene oxide and/or propylene oxide and/or epichlorohydrin.

Additionally suitable are inorganic compounds such as boric acid or boric acid salts, for example sodium metaborate, borax (disodium tetraborate), and salts of multiply charged cations, for example copper(II) salts such as copper(II) acetate or zinc, aluminum, titanium salts.

Boric acid and boric acid salts such as sodium metaborate or disodium tetraborate are suitable preferably for subsequent crosslinking. In this case, it is possible for the boric acid or boric acid salts, preferably as salt solutions, to be added to the solutions of the novel polymers. The boric acid or boric acid salts are preferably added to the aqueous polymer solutions.

The boric acid or boric acid salts can be added to the polymer solutions immediately after the preparation. However, it is also possible to add boric acid or boric acid salts subsequently to the cosmetic formulations with the novel polymers or during the process for producing the cosmetic formulations. The content of boric acid or boric acid salts, based on the novel polymers, is from 0 to 15% by weight, preferably 0 to 10% by weight, particularly preferably 0 to 5% by weight.

It is possible where appropriate for other polymers such as, for example polyamides, polyurethanes, polyesters, homo- and copolymers of ethylenically unsaturated monomers also to be present in the polymerization for preparing the novel polymers. Examples of such polymers, some of which are also employed in cosmetics, are the polymers known under the proprietary names of Amerhold™, Ultrahold™, Ultrahold Strong™, Luviflex™ VBM, Luvimer™, Acronal™, Acudyne™, Stepanhold™, Lovocryl™, Versatyl™, Amphomer™ or Eastma AQ™.

The novel comonomers (c) may, if they contain ionizable groups, be neutralized partly or completely with acids or bases before or after the polymerization, in order in this way, for example, to adjust the solubility or dispersibility in water to the required extent.

Agents which can be used for neutralizing monomers with acidic groups are, for example, mineral bases such as sodium carbonate, alkali metal hydroxides, and ammonia, organic bases such as amino alcohols, specifically 2-amino-2-methyl-1-propanol, monoethanolamine, diethanolamine, triethanolamine, triisopropanolamine, tri(2-hydroxy-1-propyl)amine, 2-amino-2-methyl-1,3-propanediol, 2-amino-2-hydroxymethyl-1,3-propanediol, and diamines such as, for example, lysine.

The K values of the polymers ought to be in the range from 10 to 300, preferably 15 to 150, particularly preferably 15 to 100, very particular preferably in the range from 20 to 80. The K value required in each case can be adjusted in a manner known per se by the composition of the starting materials. The K values are determined by the method of Fikentscher, Cellulosechemie, Vol. 13, pp. 58 to 64 and 71 to 74 (1932) in N-methylpyrrolidone or other solvents at 25° C. and polymer concentrations which are between 0.1% by weight and 5% by weight, depending on the K value range. Statement of a K value may not be worthwhile in the case of crosslinked—for example insoluble—polymers.

The ratio of the amounts of the polyethers used as grafting base and vinyl esters employed is in the range from 1:0.5 to 1:50, preferably in the range from 1:1.5 to 1:35, particularly preferably in the range from 1:2 to 1:30.

Suitable and preferred polymerization initiators are organic peroxides such as diacetyl peroxide, dibenzoyl peroxide, succinyl peroxide, di-tert-butyl peroxide, tert-butyl perbenzoate, tert-butyl perpivalate, tert-butyl peroctoate, tert-butyl permaleate, cumene hydroperoxide, diisopropyl peroxydicarbonate, bis-(o-toluoyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide and mixtures of said initiators, redox initiators and azo initiators (for example azobisisobutyronitrile, azobis(2-amidinopropane) dihydrochloride or 2,2'-azobis(2-methylbutyronitrile).

The amounts of initiator or initiator mixtures used based on the monomer employed are between 0.01 and 10% by weight, preferably between 0.1 and 5% by weight.

The polymerization takes place in the temperature range from 40 to 200° C., preferably in the range from 50 to 140° C., particularly preferably in the range from 60 to 110° C. It is normally carried out under atmospheric pressure but may also take place under reduced or elevated pressure, preferably between 1 and 10 bar.

To increase the hydrophilicity of the polymers used according to the invention it is possible for the ester groups to be hydrolyzed or partially hydrolyzed after the polymerization.

The hydrolysis takes place in a manner known per se by adding a base, preferably by adding a methanolic sodium or potassium hydroxide solution at temperatures in the range from 10 to 80° C., preferably in the range from 20 to 70° C. The degree of hydrolysis depends on the amount of base employed, on the hydrolysis temperature and on the hydrolysis time.

The degree of hydrolysis of the polyvinyl ester groups can thus be in the range from 0 to 100%. It is preferably in the range from 20 to 100%, particularly preferably in the range from 40 to 100%, especially from 65 to 100% and very particularly preferably in the range from 80 to 100%.

The solids content of the aqueous polymer dispersions or solutions obtained is ordinarily from 10 to 70% by weight, preferably 15 to 65% by weight, particularly preferably 20 to 60% by weight.

Aqueous dispersions or solutions are obtained, depending on the degree of hydrolysis and concentration, of the polymers used according to the invention.

The polymer dispersions or solutions can be converted into powder form by various drying processes such as, for example, spray drying, fluidized spray drying, drum drying or freeze drying. An aqueous dispersion or solution can be prepared anew from the dry polymer powder obtained in this way by redispersion in water. The conversion into powder form has the advantage that storability is improved, transportability is easier and the tendency to microbial attack is less.

The novel water-soluble or water-dispersible polyalkylene oxide- or polyglycerol-containing polymers are outstandingly suitable as gastric-soluble or gastric-dispersible film formers or binders, wetting excipients and/or solubilizers for pharmaceutical dosage forms and as additives for cosmetic, dermatological or hygienic preparations.

The invention further relates to cosmetic, dermatological, hygienic and/or pharmaceutical compositions comprising the novel polymers.

The following examples are intended to explain the novel preparation process in more detail:

EXAMPLE 1

| Precharge | 500 g of Pluriol E 6000 |
|---|---|
| Feed 1 | 900 g of vinyl acetate |
| Feed 2 | 8.5 g of tertiary butyl peroctoate |
|  | 100 g of Pluriol E 600 |

Apparatus 6 l JUVO vessel with anchor stirrer, 2 controlled feed vessels, nitrogen blanketing line, 1 internal thermometer (bottom), external thermometer (bath temperature measurement) and temperature control to process-control system Procedure Pressurize precharge with 9 bar of nitrogen three times. Stir precharge under 1 bar of nitrogen at 60 rpm and heat to an internal temperature of 88° C. After the precharge has reached the temperature of 88° C., feeds 1 and 2 are each added in 5 h. Feed completion is followed by polymerization at 88° C. for 3 h.

Then about 2500 g of deionized water are slowly added. Subsequently during the experiment about 400 ml of the vessel contents, essentially water and, where appropriate, monomeric vinyl acetate, are removed by vigorous introduction of nitrogen ("stripping").

Solids content 41.6%

K value 17.8 (measured as 1% strength solution in deionized water)

EXAMPLE 2

| Precharge | 51.0 g of Pluriol E 6000 |
|---|---|
| Feed 1 | 340.0 g of vinyl acetate |
| Feed 2 | 1.36 g of tertiary butyl peroctoate |
|  | 9.0 g of Pluriol E 600 |
| Feed 3 | 400 g of methanol |
| Feed 4 | 4.08 g of sodium hydroxide |
|  | 36.72 g of methanol |
| Feed 5 | 6.66 g of citric acid |
|  | 659.2 g of deionized water |

Solids content 19.8%

K value 71.1 (measured as 1% strength solution in N-methylpyrrolidone)

Apparatus 2 l Pilot stirred apparatus with anchor stirrer, reflux condenser, 2 controlled feed vessels, nitrogen blanketing, 2 internal thermometers (top and bottom), external thermometer and temperature control via process control system Procedure Stir precharge at 150 rpm under a gentle stream of nitrogen and heat to an external temperature of 90° C. After the polyethylene glycol has completely melted, 10% by weight of each of feeds 1 and 2 are added and the experiment is partially polymerized for 30 minutes. Then the remainder of each of feeds 1 and 2 is added in 3.5 h. Feed completion is followed by polymerization for 3 h.

The mixture is then cooled to 60° C., and feed 3 is added with stirring. After cooling of the experiment to below 30° C., feed 4 is added with stirring. After about 3 to 10 minutes, the hydrolysis has advanced so far that the product becomes solid (switch stirrer off if necessary). About 30 minutes after the addition of feed 4, feed 5 is added and the experiment is heated to an external temperature of 85° C. During the heating, the stirrer is switched on again. After the product has completely dissolved, the methanol (and the methyl acetate produced) is removed by steam distillation.

| Pluriol E 6000 | Polyethylene glycol with (average) molecular weight of 6000, in flake form |
|---|---|
| Pluriol E 600 | Polyethylene glycol with (average) molecular weight of 600, liquid at room temperature |

EXAMPLE 3

Preparation of Propranolol HCl Film-Coated Tablets (Enteric Coating)

9 mm biconvex tablet cores containing 40 mg of propranolol HCl (from Knoll AG), 195.0 mg of Ludipress® (from BASF Aktiengesellschaft), 12.50 mg of Kollidon® VA 64 (from BASF AG) and 2.50 mg of magnesium stearate were provided with a film coating by spraying the following com position on in a horizontal drum coater (Accela-Cota 24", from Manesty):

| | |
|---|---|
| Graft copolymer PEG 6000/VAc from Example 2 | 10.0% by weight |
| Sicovit ® red (from BASF Aktiengesellschaft) | 1.5% by weight |
| Titanium dioxide BN 56 (from Kronos) | 3.0% by weight |
| Talcum powder (from Riedel de Haen) | 4.5% by weight |
| Water | 81.0% by weight |

To prepare the spray dispersion, the graft copolymer was dissolved in water and, after addition of Sicovit® red, titanium dioxide and talcum, homogenized in a corundum disk mill. 1260 g (including an overage of 10% for spray losses) were applied to 5000 g of cores at an inlet air temperature of 60° C. and a spraying rate of 30 g/min with a 1.0 mm-wide spray nozzle and a spraying pressure of 1.5 bar. The spraying was followed by drying at 60° C. for 5 min.

Very smooth, glossy, red film-coated tablets with the following: properties were obtained:

| | |
|---|---|
| Appearance: | very smooth surface, nicely formed imprint |
| Disintegration (simulated gastric fluid): | 5 min. 11 s. |
| Disintegration time difference (film-coated tablet - core): | 42 s. |
| Hardness: | 94 N |
| Hardness difference (film-coated tablet - core): | 25 N |

COMPARATIVE EXAMPLE

In analogy to Example 3, Pharmacoat® 606 (hydroxypropylmethylcellulose, from Shin-etsu) was employed in place of the graft copolymer and, as recommended by the manufacturer's statements, 1.0% by weight of polyethylene glycol 6000 (Lutrol® 6000, BASF Aktiengesellschaft) was added.

The following tablet properties were obtained:

| | |
|---|---|
| Appearance | slightly rough surface, blurred imprint |
| Disintegration (simulated gastric fluid): | 11 min. 12 s. |
| Disintegration time difference (film-coated tablet - core): | 6 min. 43 s. |
| Hardness: | 87 N |
| Hardness difference (film-coated tablet - core): | 18 N |

EXAMPLE 4

Use as Binder in Glibenclamide Tablets 890 g of calcium hydrogen phosphate (from Rhone Poulenc) and 30 g of glibenclamide (from Arzneimittelwerk Dresden) were screened through a 0.8 mm sieve and mixed in a Turbula mixer (from Bachofen) for 5 min. This powder mixture was slowly moistened with 119 g of a 25% by weight aqueous preparation of a PEG 6000/VAc graft copolymer (prepared as in Example 2) while stirring in a Stephan mixer (from Stephan). For complete moistening the addition of the binder preparation was followed by stirring at 800 rpm for a further 2 min. The moist composition was then passed through a 0.8 mm sieve and dried on a tray at 25° C. for 20 h. Addition of 45 g of Kollidon® CL (from BASF) and 5 g of magnesium stearate (from Barlocher) was followed by final mixing, again in a Turbula mixer for 5 min. This tableting mixture was then compressed in a Korsch PH 106 rotary press (from Korsch) under a pressure of 10 kN and 18 kN to give biplanar, bevelled tablets with a diameter of 12 mm and a total weight of 500 mg.

| Properties: | 10 kN pressure | 18 kN pressure |
|---|---|---|
| Hardness: | 29 N | 55 N |
| Friability: | 0.6% | 0% |
| Disintegration: | 31 s. | 41 s. |

COMPARATIVE EXAMPLE

Production took place in analogy to Example 4 but with hydroxypropylmethylcellulose (Pharmacoat® 603, from Shin-etsu) as binder, it being necessary to reduce the binder concentration in the solution to 20% by weight for viscosity reasons.

| Properties: | 10 kN pressure | 18 kN pressure |
|---|---|---|
| Hardness: | 16 N | 40 N |
| Friability: | 8.0% | 0.6% |
| Disintegration: | 35 s. | 58 s. |

EXAMPLE 5

Use as Excipient for Producing Ultrasonic Gels 5 g of methyl p-hydroxybenzoate were dissolved in 724 g of demineralized water at 50° C. Then 6 g of polyacrylic acid (Carbopol® 940, from Goodrich) and 15 g of a 6000/VAc graft copolymer (Example 2) were incorporated with stirring. Addition of 200 g of demineralized water and 50 g of 4% strength aqueous sodium hydroxide solution was followed by stirring for 15 min, care being taken that no air was incorporated. This produced a gel with a very pleasant skin feel and good contact properties.

EXAMPLE 6

Use as Film Former in a Disinfectant Spray 150 g of a PEG 6000/VAc graft copolymer (Example 2) were dissolved in 375 g of demineralized water, and 375 g of ethanol were added. 100 g of polyvinylpyrrolidone/iodine (PVP-Jod 30/06, BASF Aktiengesellschaft) were then dissolved in this polymer solution with stirring, and the preparation was used to fill pump spray bottles. The disinfectant spray showed very good film properties on the skin and exhibited no loss of iodine after storage under stress conditions (7 days at 52° C.).

We claim:
1. A process for preparing graft copolymers of polyvinyl esters which comprises polymerizing
   a) at least one vinyl ester of aliphatic $C_1$-$C_{24}$-carboxylic acids in the presence of b) polyethers which are solid at room temperature and have the general formula I

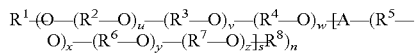

in which the variables have the following meaning, independently of one another:

$R^1$ hydrogen, $C_1$-$C_{24}$-alkyl, $R^9$—C(=O)—, $R^9$—NH—C(=O)—, polyalcohol residue;

$R^8$ hydrogen, $C_1$-$C_{24}$-alkyl, $R^9$—C(=O)—, $R^9$—NH—C(=O)—;

$R^2$ to $R^7$ —(CH$_2$)$_2$—, —(CH$_2$)$_3$—, —(CH$_2$)$_4$—, —CH$_2$—CH(CH$_3$)—, —CH$_2$—CH(CH$_2$—CH$_3$)—, —CH$_2$—CHOR$^{10}$—CH$_2$—;

$R^9$ $C_1$-$C_{24}$-alkyl;

$R^{10}$ hydrogen, $C_1$-$C_{24}$-alkyl, $R^9$—C(=O)—;

A —C(=O)—O—, —C(=O)—B—C(=O)—O—, —C(=O)—NH—B—NH—C(=O)—O—;

B —(CH$_2$)$_t$—, optionally substituted arylene;

n 1 to 8;
s 0 to 500;
t 1 to 12;
u 1 to 5000;
v 0 to 5000;
w 0 to 5000;
x 1 to 5000;
y 0 to 5000;
z 0 to 5000 c) and optionally at least one other monomer by adding a free-radical initiator system, wherein the free-radical initiator system is a solution consisting of a free-radical initiator and a liquid polyethylene glycol having a molecular weight between 88 and 1000 which polyethylene glycol is liquid at room temperature.

2. A process as claimed in claim 1, wherein the solution of the free-radical initiator is added continuously throughout the polymerization reaction time.

3. A process as claimed in claim 1, wherein liquid polyethylene glycol is used as solvent for the free-radical initiator at room temperature.

4. The process of claim 1, wherein the molecular weight of the liquid polyethylene glycol is between 100 and 600.

5. A process as claimed in claim 1, wherein the solid polyether (b) has a molecular weight of from 1000 to 500,000.

6. A process as claimed in claim 1, wherein the solid polyether (b) has a molecular weight of from 1000 to 100,000.

7. A process as claimed in claim 1, wherein the solid polyether (b) has a molecular weight of from 1000 to 20,000.

8. A process as claimed in claim 1, wherein the solid polyether (b) has a molecular weight of from 1000 to 15,000.

* * * * *